United States Patent [19]

Lewis

[11] 4,398,825
[45] Aug. 16, 1983

[54] OPTICAL SCANNER FOR BALL INSPECTION

[75] Inventor: Robert W. Lewis, Rochester, Mich.

[73] Assignee: General Motors Corporation, Detroit, Mich.

[21] Appl. No.: 234,776

[22] Filed: Feb. 17, 1981

[51] Int. Cl.³ ............................................. G01N 21/89
[52] U.S. Cl. .................................... 356/426; 356/237
[58] Field of Search ............... 356/237, 426, 445, 446, 356/448, 240, 428, 430, 431

[56] References Cited

U.S. PATENT DOCUMENTS

| | | | |
|---|---|---|---|
| 2,701,055 | 2/1955 | Strom | 356/426 |
| 3,206,606 | 9/1965 | Burgo et al. | 356/430 |
| 3,430,055 | 2/1969 | Metzger | 356/237 |
| 3,565,248 | 2/1971 | Messerschmidt | 356/426 |
| 3,565,568 | 2/1971 | Hock | 356/369 |
| 3,746,575 | 7/1973 | Arnaudin et al. | 356/237 |
| 3,822,945 | 7/1974 | Robinson et al. | 356/237 |
| 3,859,538 | 1/1975 | Mannonen | 356/430 |
| 4,037,724 | 7/1977 | Schultz et al. | 356/448 |
| 4,218,144 | 8/1980 | Whitehouse et al. | 356/446 |
| 4,259,013 | 3/1981 | Foxvog et al. | 356/237 |

FOREIGN PATENT DOCUMENTS 1343114  1/1974  United Kingdom ................ 356/430

Primary Examiner—R. A. Rosenberger
Attorney, Agent, or Firm—Warren D. Hill

[57] ABSTRACT

To inspect a ball while it is spinning, a semicircular array of balanced light sources illuminate the ball, each source being directional to illuminate a restricted zone. An array of light detectors adjacent the sources are arranged for each to detect specularly reflected light from the ball originating from a limited number of light sources and a detector channel for each detector analyzes changes in received light to detect ball surface defects. No lenses are required and the sources and detectors are formed to allow compact packaging near the ball surface.

4 Claims, 6 Drawing Figures

OPTICAL SCANNER FOR BALL INSPECTION

This invention relates to apparatus for inspecting spherical surfaces and more particularly to an optical method for inspecting balls.

It has been the previous practice to inspect the surface of a bearing ball while it is rolling down sizing rails by illuminating the ball by several light sources and attempting to detect light reflected from the ball surface by detectors positioned around the ball. Changes in the detected light level indicate the presence of defects in a surface of the ball. Apparatus previously available allowed the detection of large defects but small ones could not be found. An improvement on that arrangement has been proposed in the patent application of Faxvog et al Ser. No. 071,188 filed Aug. 30, 1979 and entitled "Optical Method for Inspecting Spherical Parts." According to that method, a lens system is used to focus light from a source onto the ball and back to a detector. Several such channels are required for complete ball inspection and while that arrangement is sensitive to small defects, alignment is critical and the required lens systems consumes much space in the ball inspection station.

It is, therefore, an object of this invention to provide a lensless apparatus for optically inspecting ball surfaces which is sensitive to small surface defects.

The invention is carried out by providing means for spinning a ball in an inspection zone, an array of balanced light sources for illuminating the ball surface, each source being directional and limited to a local area of the ball and an array of detectors each positioned to sense light specularly reflected from a small localized surface area, each detector having an electronic channel for analyzing changes in the received light to detect a ball surface defect.

The above and other advantages will be made more apparent from the following specification taken in conjunction with the accompanying drawings wherein like reference numerals refer to like parts and wherein.

Figure 1:
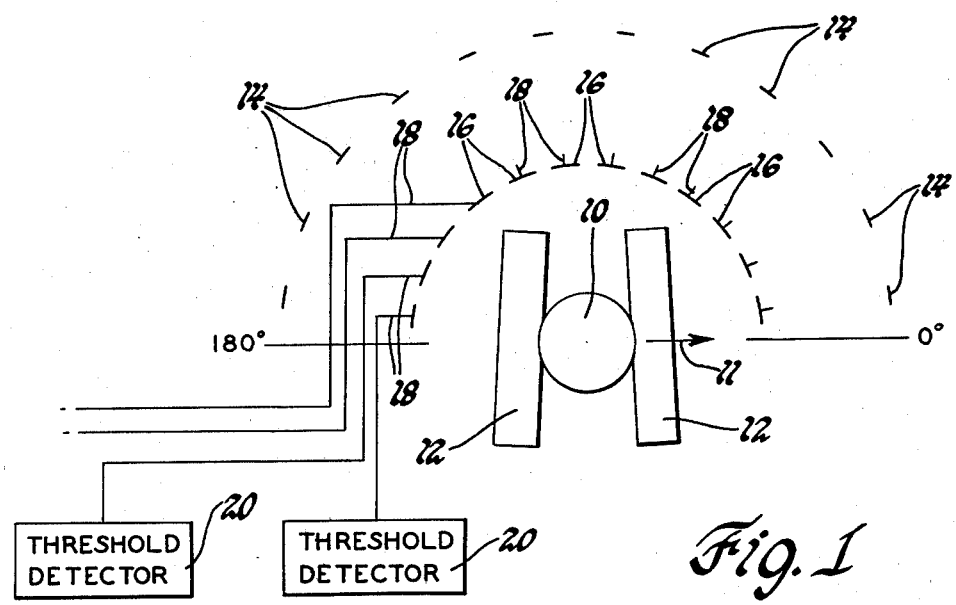
FIG. 1 is a diagrammatic illustration of an optical ball scanner according to the invention.

Referring to FIG. 1, a ball 10 to be inspected having a spin vector 11 rolls down a pair of tapered sizing rails 12 which are well known in the art of manufacturing bearing balls. The rails are set at an incline and diverge in the downward direction so that as the ball rolls down the incline between the rails, its contact with the rails moves closer to the spin axis of the ball so that the rotational velocity of the ball becomes large and its translational velocity is small. The ball is inspected as it is spinning rapidly and translating slowly. The optical ball scanner at the detection station comprises a semicircular array of light sources 14, preferably twelve in number, the array being concentric with the ball 10, and an array of detectors 16 equal in number to the light sources, the detector array also being concentric with the ball but in a different plane than the source array. In FIG. 1 the detectors 16 and sources 14 are shown only as dashes in order to simplify the drawing. Each of the detectors 16 has an electrical output line 18 each of which is connected to a separate threshold detector 20. Each detector 16 inspects a portion of the ball surface centered directly beneath it. Each detector intercepts light originating from more than one source. An output signal on each line 18 is proportional to the total light received by the respective detector. Each detector signal is processed separately by a separate channel or threshold detector 20. A smooth ball surface reflects a constant amount of specular light to the detectors but a defect absorbs or scatters light to cause a momentary dip in a detector output. The detector 20 senses the signal change by level detection or signal rate of change detection.

Surface noise consisting of surface irregularities not classified as defects limit the size of the smallest detectable defect (scanner sensitivity). Scanner sensitivity can be improved if light sources and/or detectors possessing narrow precisely controlled directional characteristics are employed. This permits a closer realization of the ideal condition that each detector receive only the specular component of the reflected light originating from its three nearest sources, and that the contribution of all other sources to the detector signal be zero. Such directional components reduce surface noise by decreasing the area of each detector's surface coverage inspection zone, and by decreasing the amount of scattered light reaching a detector from illuminated surface areas outside each detector channel's required surface coverage zone. Directional sources, in addition, reduce the amount of detected scattered light which is generated within a detector's required surface coverage inspection zone.

Figure 2:
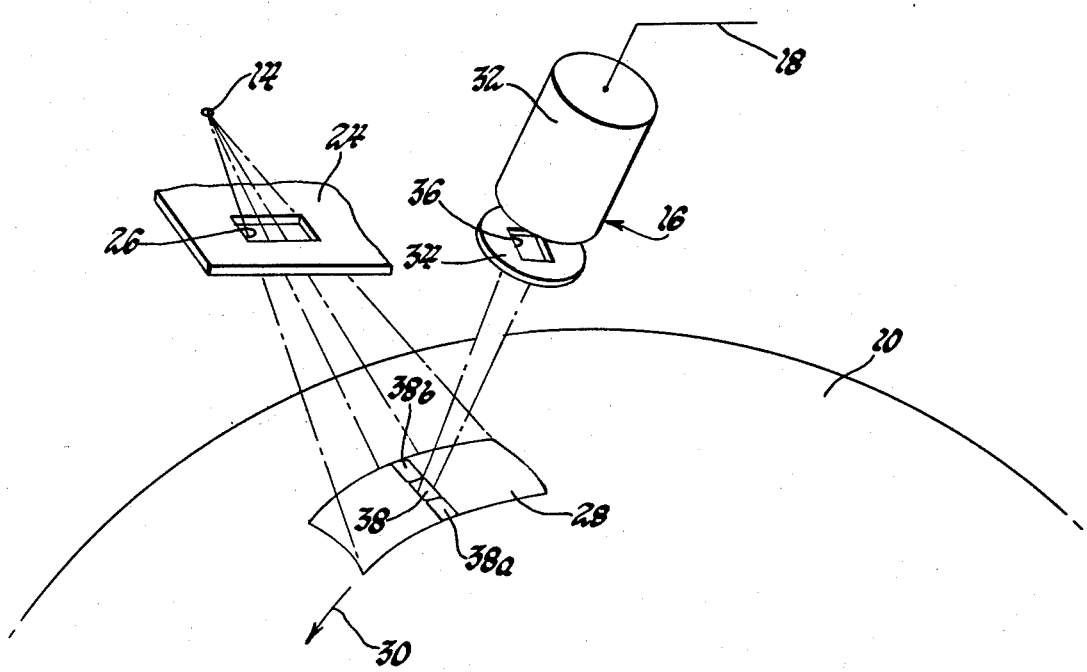
FIG. 2 is a schematic view of a portion of the scanner of FIG. 1 showing the optical relationship between a single source and a single detector.
Figure 3:
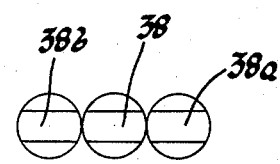
FIG. 3 is a diagrammatic view of ball surface illumination indicating the coverage obtained by a single detector.

FIG. 2 illustrates the illumination of a restricted zone of a ball 10 by a directional source and the coverage of a portion of that zone by a detector. The source comprises a point source 14 or very small lamp spaced from a mask 24 containing a rectangular aperture 26. The light projected through the aperture 26 forms a defined illumination zone 28 on the surface of the ball 10. The ball surface is moving in rotation along the direction of the arrow 30 and the long dimension of the rectangular zone 28 is aligned with the direction of rotation so that the area beneath the detector 16 will be illuminated even though the ball translates slightly while it is spinning. The detector 16 comprises a phototransistor 32 and a mask 34 containing an aperture 36 immediately in front of the phototransistor. The aperture 36 defines the specific area of 38 to the ball 10 viewed by the detector 16. Thus while the light from the source 14 illuminates the large zone 28 on the ball 10 only that light specularly reflected from the small area 38 passes through the aperture 36 to the phototransistor 32. The detectors immediately adjacent that in FIG. 2, though not shown, also receive some of the light specularly reflected from the ball from the illumination zone 28. That is, the small areas 38a and 38b on either side of the area 38 are viewed by one or the other of the adjacent detectors. Similarly, each detector receives light from adjacent sources. The number of sources producing specular light received at a given detector is limited by the narrow dimension of each zone 28. Thus, the sources immediately neighboring the source 14, in FIG. 2, illuminate areas 38a and 38b of the ball on each side of the area 38 and light specularly reflected therefrom passes into the detector 16. As shown in FIG. 3, the three circles represent areas on the ball surface within the illuminated zone 28 which would, in the absence of the mask 34, be viewed by the detector 16. The mask 34, however, has the effect of reducing the scanner coverage in one direction so that areas 38, 38a and 38b are viewed, the three images being received from three separate adjacent sources 14. A defect passing through any of the areas 38, 38a or 38b reduces the light received by the detector to change the signal level on its output line 18. Reducing the scanner coverage by mask 24 increases the sensor sensitivity to small defects. The combined coverage of all the detectors is a nearly continuous viewing area forming a strip across the ball.

Figure 4:
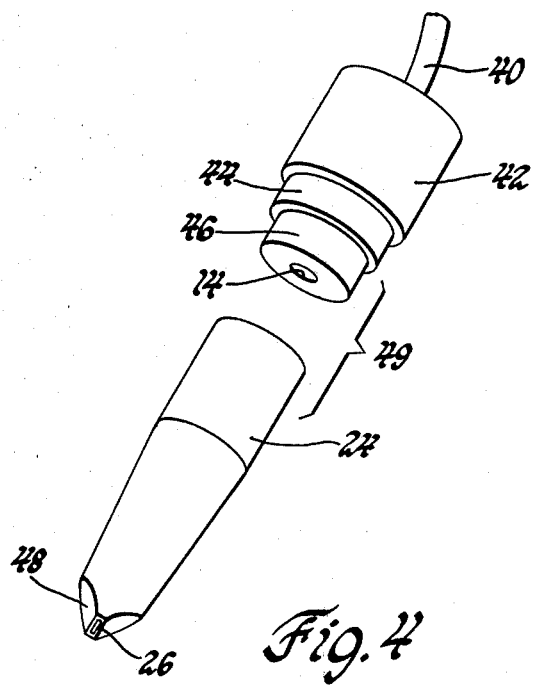
FIG. 4 is an exploded view of a fiber optic light source and aperture combination.
Figure 5:
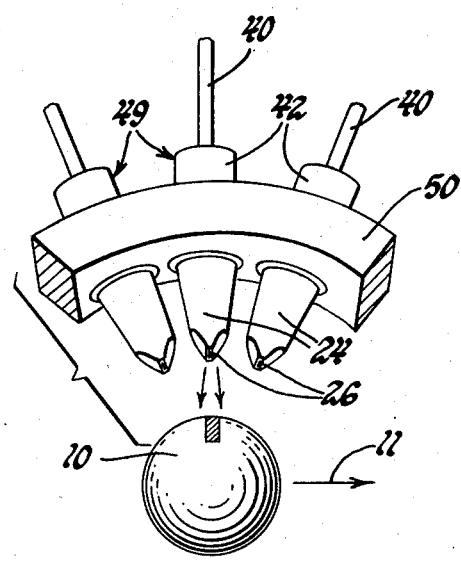
FIG. 5 is an isometric view of a portion of an array of apertured light sources adjacent a ball.

FIGS. 4 and 5 illustrate the directional light source and the grouping of light sources adjacent a ball 10. The point source 14 of FIG. 2 is represented by the end of a plastic optical fiber 40 which is accurately held in the bore of a brass ferrule 42 secured to the end of the fiber 40. To achieve a small area of light emission, only a single fiber is utilized. The ferrule 42 is cylindrical and has reduced diameter steps 44 and 46 adjacent the end thereof. A copper terminal or mask 24 is a hollow tapered or truncated cone shaped element terminating in a wedge point 48 having a rectangular slit aperture 26. The terminal 24 has blackened inner walls and the small amount of light which reflects off these walls is dispersed by the wall taper. The shape of the terminals 24 permits them to be closely positioned near the ball surface as illustrated in FIG. 5. The small diameter surface 46 of the ferrule is dimensioned to snuggly fit within a mating cavity in the terminal 24 thereby accurately positioning the light source 14 with respect to the aperture 26. The combination of the optical fiber 40, the ferrule 42 and the mask 24 comprise a source assembly 49.

An arcuate source holder 50, a segment of which is shown in FIG. 5, has accurately formed holes for positioning the source assemblies 49 to properly illuminate the surface of the ball 10. The apertures 26 are oriented so that the slits are parallel to the direction of ball translation. This permits the ball scanner to track a ball through at least one ball revolution during inspection. The size of the aperture 26 in the mask is chosen so that in the aggregate the twelve sources will illuminate a continuous strip around half the ball except at the spin axis regions and yet each source illuminates a limited area to provide specular light to primarily the three nearest detectors.

In an apparatus specifically designed to inspect 6 mm diameter balls light guides 1 mm in diameter are used for light sources 14. The apertures 26 are 1 mm by 2 mm openings which are positioned 8 mm from the source 14 and 5 mm from the ball surface. The required width of the illuminated zone 28 is on the order of 1 mm, however, in practice the light source provides a somewhat larger illuminated area. The important parameter is that the intensity of the illumination throughout the zone 28 is uniform and the intensity rapidly falls off outside the zone 28. The net result is that the three adjacent detectors which are primarily illuminated by one source are evenly illuminated thereby and that other more distant detectors receive much lower levels of specular light from the one source. Each detector 16 is spaced about 6 mm from the surface of the ball and receives specular light from spots 38, 38a and 38b each about 0.35 mm in width. The height of the spots is controlled by the width of the aperture 36 at the detector. For a 1 mm wide aperture painted on the face of the phototransistor lens, the effective height of the spot 38 is 0.2 mm.

Figure 6:
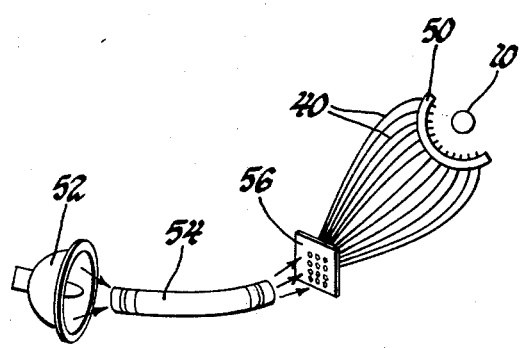
FIG. 6 is a schematic view of a fiber optic balanced illumination system according to the invention.

To provide balanced illumination to the detectors from the various sources, it is important that the sources have substantially equal output. This is accomplished, as shown in FIG. 6, by a quartz-halogen lamp 52 having a reflector for focusing its light onto one end of a noncoherent fiber optic light guide 54. This light guide consists of a large number of small glass fibers which have a random spatial relationship at each end. The output light from the guide 54 uniformly illuminates the ends of the twelve optical fibers 40 which are packed closely together in a matrix and held in place by a matrix plate 56 having an aperture for each optical fiber 40. The illuminated ends of the fibers 40 are frosted by abrasion with emery cloth. The noncoherent light guide 54 provides a means for illuminating the matrix of fibers 40 with an intense uniform beam of light without overheating the plastic fiber. The random nature of the guide 54 together with the fact that the matrix of fiber ends are frosted ensures that the relative light outputs of the plastic fibers is not affected by lamp replacement. Further if a fiber 40 is illuminated off axis a null can occur at the center of its light output pattern which reduces the light output from a fiber's exit aperture. Frosting the ends of the fibers 40 helps eliminate this problem and produces a very uniform fiber light output pattern. A 150 watt lamp excites the optical source systems sufficiently to produce 0.1 mw light through each aperture 26. The scanner operates well even at lower light levels than this.

Because mechanical stress and bending affects a fiber's light transmittance, the light output of the fibers must be balanced after the source array is inserted into the fixture 50. A fiber's transmittance can be precisely adjusted by filing shallow notches into the fiber wall. Because of the nature of light propagation through a fiber, several notches produce a multiplicative effect in decreasing a fiber's transmittance. Adjustment points can be strengthened with black epoxy without changing the adjusted transmittance.

The measured detection responses of the optical ball scanner described above reveal that a 0.2 mm diameter surface defect is detectable on a 6 mm diameter ball. It will thus be seen that a ball scanner according to this invention is very sensitive to defects in bearing balls and requires no expensive or fragile lens systems which are subject to dirt accumulation during operation in a manufacturing facility and which are difficult to package into the small space necessary for the inspection of a small ball. Alignment of the system elements and the scanner relative to the sizing rails is not as critical as in a lens system.

The embodiments of the invention in which an exclusive property or privilege is claimed are defined as follows:

1. An optical scanner for optically inspecting the surface of balls comprising;
    means for spinning a ball to be inspected, a semicircular array of substantially equal intensity light sources for illuminating the ball surface, each light source being directional to illuminate a restricted zone of the ball,
    a semicircular array of light detectors adjacent the array of sources, each detector being positioned to sense the light specularly reflected from several discrete surface areas proximate the detector and originating from several light sources adjacent the detector, whereby substantially no light from remote zones of the ball reaches the said detector, and a plurality of electronic detector channels, one for each light detector, for analyzing changes in received light to determine the presence of a ball surface defect.

2. An optical scanner for optically inspecting the surface of balls comprising;

means for spinning a ball to be inspected, a semicircular array of substantially equal intensity light sources for illuminating the ball surface comprising a plurality of optical fibers each having an input end and an output end, the input ends being close together and the output ends being separated for emitting light at spaced points, a lamp, a noncoherent fiber optic light guide having one end illuminated by the lamp and the other end arranged to evenly illuminate the input ends of the optical fibers, each light source being directional to illuminate a restricted zone of the ball, a semicircular array of light detectors adjacent the array of sources, each detector being positioned to sense the light specularly reflected from several discrete surface areas proximate the detector and originating from several light sources adjacent the detector, whereby substantially no light from remote zones of the ball reaches the said detector, and a plurality of electronic detector channels, one for each light detector, for analyzing changes in received light to determine the presence of a ball surface defect.

3. An optical scanner for optically inspecting the surface of balls comprising;

means for spinning a ball to be inspected, a semicircular array of substantially equal intensity directional light sources for illuminating the ball surface, each light source comprising an illuminated optical fiber for emitting light from an end thereof and an aperture positioned between the said end and the ball to limit illumination to a restricted zone of the ball, a semicircular array of light detectors adjacent the array of sources, each detector being positioned to sense the light specularly reflected from several discrete surface areas proximate the detector and originating from several light sources adjacent the detector, whereby substantially no light from remote zones of the ball reaches the said detector, and a plurality of electronic detector channels, one for each light detector, for analyzing changes in received light to determine the presence of a ball surface defect.

4. An optical scanner for optically inspecting the surface of balls comprising;

means for spinning a ball to be inspected, a semicircular array of substantially equal intensity light sources for illuminating a strip across the ball surface, each light source being directional to illuminate a restricted zone of the ball, a semicircular array of light detectors adjacent the array of sources, each detector being positioned to sense the light specularly reflected from several discrete surface areas proximate the detector and originating from several light sources adjacent the detector, whereby substantially no light from remote zones of the ball reaches the said detector, each detector having an entrance aperture to define the size and shape of the said several discrete surface areas, the discrete surface areas in aggregate forming a substantially continuous band within the illuminated strip across the ball surface, and a plurality of electronic detector channels, one for each light detector, for analyzing changes in received light to determine the presence of a ball surface defect.

* * * * *